United States Patent [19]
Strobel et al.

[11] Patent Number: 5,693,291
[45] Date of Patent: Dec. 2, 1997

[54] REAGENTS KIT FOR THE QUANTITATIVE ANALYSIS OF PROTEINS OR/AND PEPTIDES

[75] Inventors: Oliver Strobel; Edith Strobel, both of Benediktbeuren; Herbert Von der Elt, Weilheim, all of Germany

[73] Assignee: Boehringer Mannheim GmbH, Mannheim, Germany

[21] Appl. No.: 703,664

[22] Filed: Aug. 27, 1996

[30] Foreign Application Priority Data

Aug. 28, 1995 [DE] Germany .......................... 295 13 801 U
Sep. 7, 1995 [DE] Germany .......................... 295 14 396 U

[51] Int. Cl.$^6$ ................................................ G01N 33/483

[52] U.S. Cl. ...................... 422/61; 436/86; 436/166; 436/808

[58] Field of Search .......................... 422/61; 436/15, 436/86, 164, 166, 808

*Primary Examiner*—Lyle A. Alexander
*Attorney, Agent, or Firm*—Nikaido, Marmelstein, Murray & Oram LLP

[57] ABSTRACT

The invention relates to a reagents kit for the quantitative analysis of proteins or/and peptides, comprising a reagent A containing 0.7 to 2 mmol/l $Cu^{2+}$ ions and 2 to 4 mmol/l tartrate in alkaline solution and a reagent B containing 1 to 1.5 mmol/l ascorbic acid and 0.5 to 0.8 mmol/l bathocuproine, with the proportion by volume of reagent A to reagent B being 1:8 to 1:12 and the joint volume of reagent A and reagent B being between 750 μl and 3000 μl.

11 Claims, 2 Drawing Sheets

REAGENTS KIT FOR THE QUANTITATIVE ANALYSIS OF PROTEINS OR/AND PEPTIDES

The invention relates to a reagents kit for the quantitative analysis of proteins or/and peptides.

Proteins represent a large and important group of biomolecules. On account of their wide distribution and the central role they play in nature, numerous techniques have been developed for measuring protein concentrations. The currently most often used spectrophotometric techniques can be divided into two groups based on the methods of obtaining a coloured and thus detectable solution.

Copper-chelating-agent assays make use of a copper-protein complex formation under strongly basic conditions, the so-called biuret reaction, for detection.

Dye-protein complex formations serve as means of detection in a second group, with the dye-protein complex formation effecting a shift in the absorption maximum of the dye.

The technique developed by Lowry et al. (Lowry, O. H., Rosebrough, N. J., Farr, A. L., and Randall, R. J. (1951) J. Biol. Chem. 193, 265–275) involves the use of Folin-Ciocalteau reagent to increase the senstitivity of the biuret reaction. This results in a relatively high level of sensitivity (0.2 to 1.4 mg/ml). This technique also boasts a relatively high degree of stability and repeatability with different proteins. A serious disadvantage of the technique, however, is the instability of the detection reagent under alkaline conditions.

The technique according to Smith et al., (Smith, P. K., Krohn, R. I., Hermanson, G. T., Mallia, A. K. Gartner, F. H., Provenzano, M. D., Fujimoto, E. K., Goeke, N. M., Olson, B. J. and Klenk, D. C. (1985) Anal. Biochem. 150, 76–85) likewise involves use of the biuret reaction for the determination of proteins. As copper chelating agent use is made of bicinchonine acid (BCA), which, together with copper ions, forms a detectable lilac-coloured complex.

This assay is characterized by a high level of sensitivity (0.1 to 1 to 2 g/ml) and reagents which are highly stable. However, there are large protein-to-protein fluctuations with different proteins.

Of the dye-protein complex assay group, the most widely used is the Bradford protein assay (Bradford, M. M. (1976) Anal. Biochem. 72, 248–254). In this assay use is made of Coomassie brilliant blue 250 as complexing dye. This assay too shows a relatively high level of sensitivity (0.2 to 1.4 mg/ml) but has the disadvantages of high protein-to-protein fluctuations with different proteins and susceptibility towards detergents and alkaline buffers.

Another copper chelate protein assay has been described by Matsushita et al., (Matsushite, M., Irino, T., Komoda, T. and Sakagishi, Y. (1993) Clin. Chim. Acta 216, 103–111). This technique also involves use of the biuret reaction for determining protein concentrations. For detection thereof, however, excess $Cu^{++}$ is reduced to $Cu^+$ and the coloured bathocuproine-$Cu^+$ complex is determined. This technique has a low protein-to-protein variability and the reagents are highly stable. Disadvantageous, however, is the sensitivity limit of of 0.4 mg/ml. The technique also has a number of disadvantages which make it difficult to carry out as a standard protein assay. The incubation temperature, for example, is 37° C., which makes handling more difficult, and the total volume in this technique is not suitable for carrying out the protein assay in standard semi-microcells.

The object of this invention was thus to provide a reagents kit for determining proteins, which at least partially overcomes the disadvantages of the prior art.

The object is established according to the invention by provision of a reagents kit for the quantitative analysis of proteins or peptides, comprising a reagent A containing $Cu^{2+}$ ions and tartrate in alkaline solution and a reagent B containing ascorbic acid and bathocuproine, the proportion by volume of reagent A to reagent B being 1:8 to 1:12 and the joint volume of reagent A and reagent B being between 750 µl and 3000 µl.

The object is established in particular by provision of a reagents kit for the quantitative analysis of proteins and peptides, comprising a reagent A containing 0.7 to 2 mmol/l $Cu^{++}$ ions and 2 to 4 mmol/l tartrate in alkaline solution and a reagent B containing 1 to 1.5 mmol/l ascorbic acid and 0.5 to 0.8 mmol/l bathocuproine, the proportion by volume of reagent A to reagent B being 1:8 to 1:12 and the joint volume of reagent A and reagent B being between 750 µl and 3000 µl.

With the reagents kit of the invention, protein and peptide concentrations can be determined spectrophotometrically. Addition of reagent A to a sample solution containing a protein results first of all in formation of a copper-protein complex analogous to the biuret reaction. After an incubation period, reagent B is added. Excess $Cu^{++}$ ions are reduced by a reducing agent such as ascorbic acid to $Cu^+$ ions. The $Cu^+$ ions, together with a complexing agent such as bathocuproine which is likewise contained in reagent B, form a coloured complex the absorption of which can be measured. The signal thus obtained is inversely proportional to the number of peptide bonds and, unlike other conventional protein assays, is independent of the amino acid side groups.

The reagents kit of the invention makes it possible to obtain accurate and sensitive measurements of protein and peptide concentrations. By virtue of the low protein-to-protein variability it is also possible to measure protein mixtures very accurately. Further advantages of protein determination with the reagents kit of the invention are the short assay time, highly stable reagents, excellent sensitivity, a wide linear range and non-susceptibility towards substances which might otherwise interfere.

It is of advantage if the reagents kit contains copper sulfate and/or sodium potassium tartrate in reagent A. $Cu^{++}$ ions and tartrate can also be used, however, in other forms familiar to persons skilled in the art. Reagent B contains a reducing agent, preferably ascorbic acid, and a complexing agent, preferably bathocuproine disulfonic acid disodium salt. In principle, however, all complexing agents that form a complex with copper under alkaline conditions are suitable.

The concentration of $Cu^{++}$ ions in reagent A is preferably within the range from 0.8 to 1.2 mmol/l, with a concentration of 0.86 mmol/l being particularly preferred. Reagent A also contains tartrate in a preferred concentration of 2 to 2.5 mmol/l, with a concentration of 2.28 mmol/l being particularly preferred. In addition, reagent A preferably also contains a base, for example NaOH in a concentration of 700 to 1000 mmol/l.

Reagent B contains a reducing agent preferably in a concentration within the range from 1.3 to 1.35 mmol/l, with a concentration of 1.32 mmol/l being particularly preferred. The concentration of the complexing agent contained in reagent B is preferably within the range from 0.6 to 0.64 mmol/l, with a concentration of 0.62 mmol/l being particularly preferred.

So that the protein assay can be performed without complications using normal laboratory apparatus, the protein assay volume is selected to allow the use of standard semi-microcells or standard microcells. Standard semi-microcells are preferred, with the total volume of the reagents being between 900 µl and 1500 µl.

The reagents kit of the invention preferably also contains a buffer solution with which standard and sample solutions can be prepared. In addition, the reagents kit preferably contains a standard protein solution. It is of advantage if the standard protein solution has a concentration within the range from 20 µg/ml to 2 mg/ml. It is preferable if the reagents kit contains a more highly concentrated protein stock solution from which suitable standard solutions can be prepared by way of dilution. Of particular advantage is a protein stock solution containing bovine serum albumin in a concentration of 2 mg/ml. For an assay, the suitably diluted standard protein solution is used preferably in a proportion by volume of 1:1.6 to 1:2.4 relative to reagent A.

The reagents kit of the invention and the corresponding assay procedure are distinguished especially by easy handling, by the fact that the quantitative analysis of proteins and peptides is easy to carry out, that there is little protein-to-protein variability and by a low detection limt.

The procedure on which the assay is based and which as such is a familiar one comprises three steps. In the first step, sample solution containing proteins or peptides is reacted with alkaline $Cu^{++}$-tartrate solution, as a result of which a $Cu^{++}$-protein complex is formed. In the second step excess $Cu^{++}$ is reduced to $Cu^{+}$ with a reducing agent, in particular ascorbic acid. This $Cu^{+}$, together with a complexing agent such as bathocuproine or another complexing agent stable towards alkalis, subsequently forms a coloured complex which serves for quantitative detection. For the assay procedure, reagent A contains the reagents for the first step (reaction 1) while reagent B comprises the reagents for the second and third steps (reaction 2). The assay volume according to the invention is 750 to 3000 ml, with sample volumes of 15 of 15 to 150 µl being used.

The total volume of an assay is selected such that the assay can be carried out in standard cells. This means the assay can be performed with the usual laboratory materials, without the need for expensive special apparatus. It is preferable if the assay is carried out in standard semi-microcells, with the detection reactions being able to take place entirely in one cell. The total assay volume is preferably in the range from 900 to 1500 µl.

The assay can be carried out at 37° C., but this necessitates preliminary heating of the preparation. It is preferable to carry out the assay at room temperature, thus rendering heat-regulation measures unnecessary and making for considerably easier handling.

The development of detectable colour in reaction 2 depends on the incubation time selected for reaction 2. In order to obtain reproducible and comparable results, it is necessary to measure the absorption after a given incubation time for reaction 2. Surprisingly, it was found that when the concentrations and volumes according to the invention are used, a change from 5 to 70 minutes in the incubation time for reaction I does not alter the results. This represents an additional important simplification in the procedure, since with reaction 1 not being time-dependent, reaction 2, which is time-dependent, can be started at a time which suits the user. Moreover, this means that a sample can be prepared and measured in just 7 minutes.

When concentrations according to the invention are used, the assay is distinguished by a very low detection limit: concentrations as low as 20 µg protein or peptide per ml of sample solution can be measured. The linear range is dependent on the concentrations of the reagents. Changing the concentrations of the reagents changes the linear range but also the detection limit. Thus, depending on the particular requirements, one can optimize the detection limit or obtain as large a linear range as possible by making use of suitable concentrations.

The sample volume used in an assay is preferably 15 to 150 µl. With the added advantage of the low detection limit, this means that many protein- or peptide-containing liquids to be analysed can be used directly, without the necessity of their first having to be concentrated. Of particular importance is the fact that for example protein or peptide solutions that have been cleared on columns do not need to be freed of excess solvent prior to determining the protein concentration.

It is furthermore possible, using the assay described here, to measure various proteins without large fluctuations. A low protein-to-protein variability is important especially for the measurement of different proteins or of mixtures of proteins. The protein assay described here shows little protein-to-protein variability, which means that various different proteins can be accurately quantified.

The protein assay is characterized in addition by the excellent compatibility of the reagents, thus largely excluding the possibilitiy of interference by sample impurities, buffers or supplementary agents.

Since not only proteins but also peptides can be analyzed quantitatively with the reagents kit described here, it has a wide range of application.

The assay can be automated by carrying it out on microtiter plates, in which case the volume for one cell is divided up among 10 wells. The protein assay is furthermore suitable for the quantitative analysis of immobilized proteins such as those bound to a solid matrix, e.g. agarose.

The invention is explained in more detail with the following examples:

EXAMPLE 1

Standard Assay Procedure/Preparation of a Calibration Curve

Reagent A, comprising 0.86 mM $CuSO_4 \times 5H_2O$, 2.28 mM sodium potassium tartrate and 0.86 NaOH and reagent B, comprising 1.32 mM ascorbic acid and 0.62 mM bathocuproine disulfonic acid disodium salt are heated to room temperature or 37° C. A series of standard solutions covering the concentration range to be measured is made up by diluting the BSA standard protein solution contained in the reagents kit to 0, 50, 100, 300, 500 and 750, 1000, 1500 and 2000 µg/ml.

Figure 1:
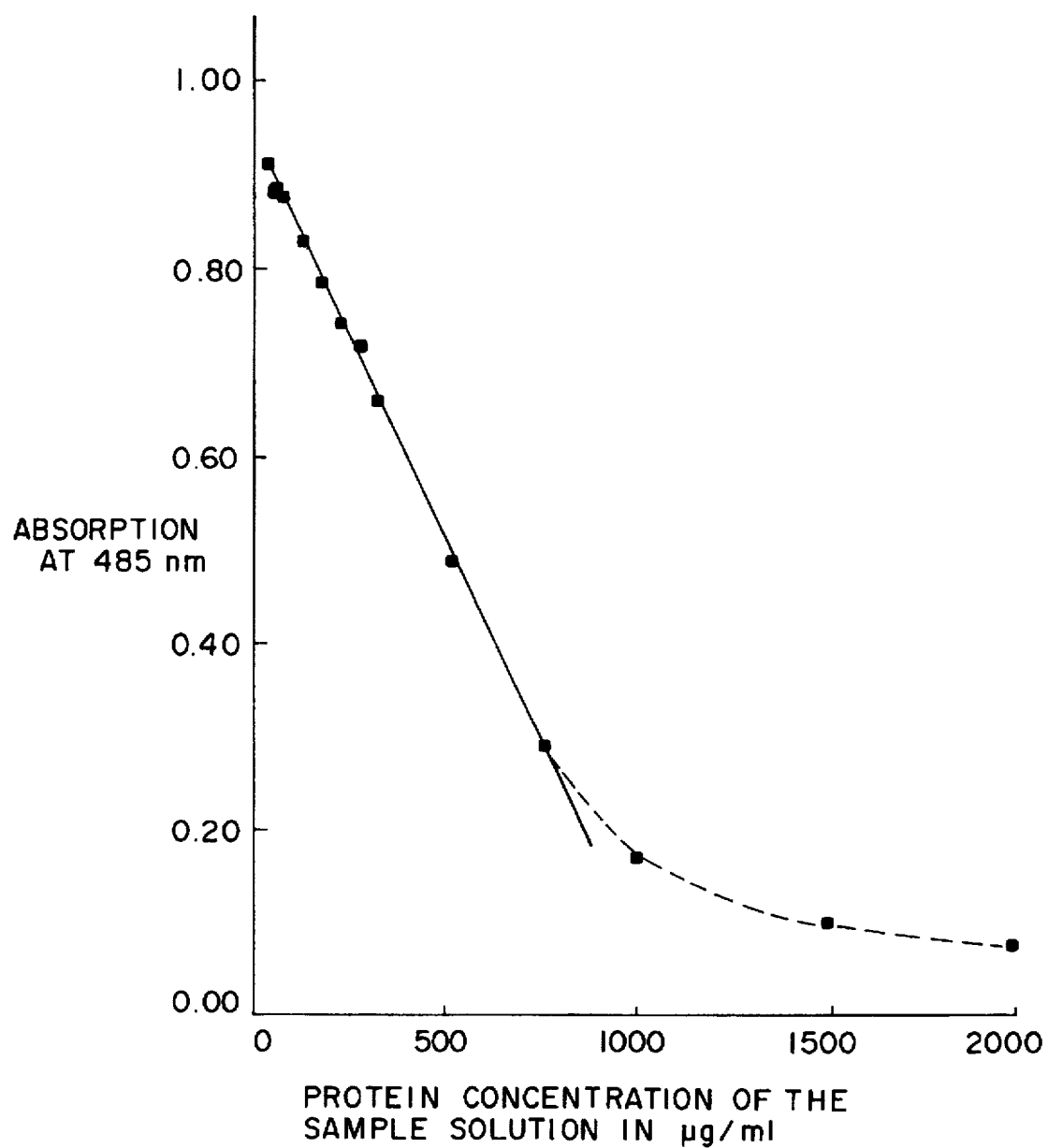
FIG. 1 illustrates a calibration curve obtained by example 1 with BSA.

100 µl of reagent A are introduced into a semi-microcell (1.5 ml). 50 µl of standard solution or of sample solution are then added to the cell and mixed with reagent A. The solutions are incubated at room temperature for at least 5 minutes. Longer incubation periods of up to 1 hour do not influence the results of the protein assay. Subsequently 1000 µl of reagent B are added to the cell and mixed briefly. After 30 seconds the absorption at 485 nm is measured. A calibration curve obtained with BSA is shown in FIG. 1. The assay has a linear range from 20 to 800 µg protein per ml sample solution (absolute: 1 to 40 µg protein per assay).

Using a calibration curve of this kind, the protein concentrations of unknown samples can be calculated. In the case of repeated measurements taken on samples having the same matrix it usually suffices to prepare a calibration curve just once and then simply to check the validity of this calibration curve at a single point, e.g. at zero.

EXAMPLE 2

Linear Range/Change in Concentrations of the Reagents

A protein assay is carried out as in Example 1, with reagent A containing 1.1 mmol/l copper sulfate and 2.9 mmol/l potassium sodium tartrate. In this way it is possible to extend the linear range in the assay to 100 to 1500 µg protein per ml sample solution.

EXAMPLE 3

Linear Range/Change in the Concentrations of the Reagents

A protein assay is carried out as in Example 1, with reagent A containing 1.3 mmol/l copper sulfate and 3.4 mmol/l potassium sodium tartrate. In this way it is possible to extend the linear range in the assay to 100 to 1700 µg protein per ml sample solution.

EXAMPLE 4

Incubation Time of the First Reaction

The protein assay was carried out as in Example 1, with incubation times for the first reaction of 5, 20 and 70 minutes at room temperature. No change in resuls was observed as a result of the differrent incubation times for the first reaction.

EXAMPLE 5

Temperature Dependence

The protein assay was carried out as in Example 1 at room temperature and at 37° C. No change in the linear range and the lower detection limit was observed at the different temperatures. Carrying out the assay at room temperature makes handling considerably easier.

EXAMPLE 6

Protein-to-Protein Variability

Figure 2:
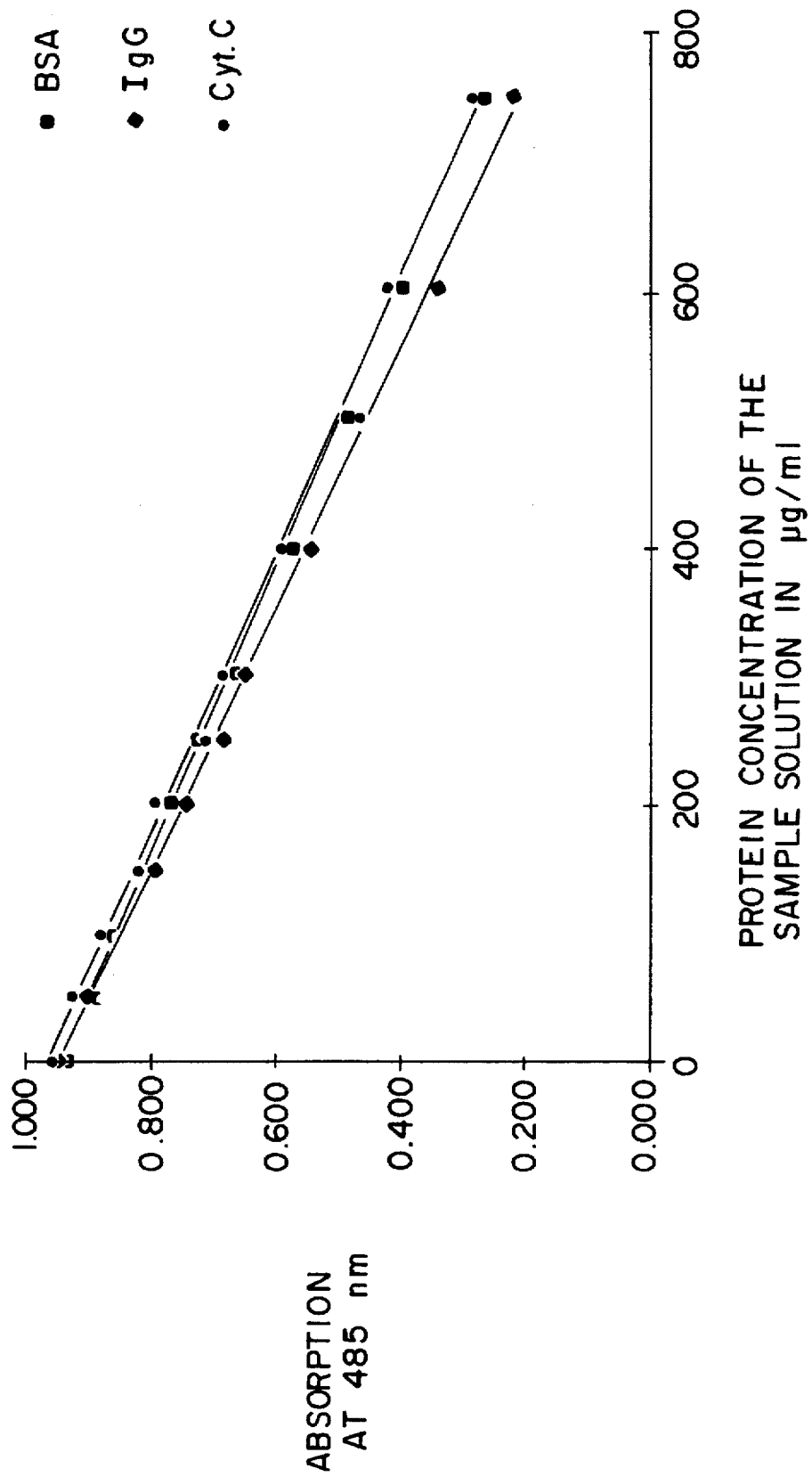
FIG. 2 illustrates the results of example 6 that show there is vert slight variation with different proteins.

The assay was tested on samples of mouse immunoglobulin-G, horse cyto-chrome C and beef serum albumin. The results documented in FIG. 2 prove that there is only a very slight variation with different proteins.

EXAMPLE 7

Compatibility of the Reagents

The assay was carried out as in Example 1. Combinations of substances as shown in the following table were added to the standard protein solutions. No change in results was observed, which demonstrates the non-susceptibility of the procedure towards buffers and other additives.

| | | |
|---|---|---|
| 1% octylglucosidase (w/v) | 0.5M HEPES, pH 5.1 | 0.5M ammonium sulfate |
| 0.5% Triton ® X-100 w/v | 0.5M sodium phosphate, pH 7.5 | 0.5M ammonium acetate |
| 0.5% Brij ® 35 (w/v) | 0.1M glycine, pH 2.8 | 0.1% Micr-O-Protect (v/v) |
| 0.5% Thesit ® (w/v) | | 5 mM $CaCl_2$ |
| 0.5% Nonidet ® P-40 (w/v) | | 0.2 mM DTT |
| 0.5% CHAPS (w/v) | | 0.1% sodium azide (w/v) |

We claim:

1. A reagents kit for the quantitative analysis of at least one of proteins and peptides comprising a reagent A containing 0.7 to 2 mmol/l $Cu^{2+}$ ions and 2 to 4 mmol/l tartrate in alkaline solution and a reagent B containing 1 to 1.5 mmol/l ascorbic acid and 0.5 to 0.8 mmol/l bathocuproine, the proportion by volume of reagent A to reagent B being 1:8 to 1:12 and the joint volume of reagent A and reagent B being between 750 µl and 3000 µl.

2. A reagents kit as claimed in claim 1, wherein
   reagent A contains $CuSO_4$ and sodium potassium tartrate.

3. A reagents kit as claimed in claim 1, wherein
   reagent B contains bathocuproine disulfonic acid disodium salt.

4. A reagents kit as claimed in claim 1, wherein
   reagent A contains $Cu^{2+}$ in a concentration of 0.8 to 1.2 mmol/l and tartrate in a concentration of 2 to 2.5 mmol/l.

5. A reagents kit as claimed in claim 1, wherein
   reagent B contains ascorbic acid in a concentration of 1.3 to 1.35 mmol/l and bathocuproine in a concentration of 0.6 to 0.64 mmol/l.

6. A reagents kit as claimed in claim 1, wherein
   the total volume of the reagents is between 900 µl and 1500 µl.

7. A reagents kit as claimed in claim 1, wherein
   said reagents kit contains a buffer solution.

8. A reagents kit as claimed in claim 1, wherein
   said reagents kit contains a standard protein solution.

9. A reagents kit as claimed in claim 1, wherein
   the concentration of the standard protein solution is 20 µg/ml to 2 mg/ml.

10. A reagents kit as claimed in claim 1, wherein
    the proportion by volume of standard protein solution to reagent A for an assay is 1:1.6 to 1:2.4.

11. A reagents kit as claimed in claim 1, wherein
    said reagents kit contains a bovine serum albumin solution as standard protein solution.

* * * * *